United States Patent [19]

Zinnen

[11] Patent Number: 4,992,621
[45] Date of Patent: Feb. 12, 1991

[54] SEPARATION OF COUMARONE FROM INDENE

[75] Inventor: Hermann A. Zinnen, Evanston, Ill.

[73] Assignee: UOP, Des Plains, Ill.

[21] Appl. No.: 412,951

[22] Filed: Sep. 26, 1989

[51] Int. Cl.⁵ .............................................. C07C 7/13
[52] U.S. Cl. .................................... 585/826; 585/827; 585/828; 208/310 Z
[58] Field of Search ............... 585/822, 824, 826, 827, 585/828; 208/310 R, 310 Z

[56] References Cited

U.S. PATENT DOCUMENTS 2,621,203  12/1952  Cope .............................. 585/826 X Primary Examiner—Curtis R. Davis
Assistant Examiner—William Diemler
Attorney, Agent, or Firm—Thomas K. McBride; John F. Spears, Jr.; Jack H. Hall

[57] ABSTRACT

The chromatographic adsorption separation of coumarone from indene-containing coal tar distillate feed mixtures with an alkali metal (Group IA) exchanged X-zeolite and polar materials, e.g., ketones, alcohols or esters as desorbents. Also disclosed is a process for separating a coumarone-indene coextract with sodium-exchanged Y zeolite and toluene as desorbent.

16 Claims, 4 Drawing Sheets

SEPARATION OF COUMARONE FROM INDENE

FIELD OF THE INVENTION

The field of art to which this invention pertains is solid-bed adsorptive separation, more specifically, to an improved process for separating coumarone from coal tar distillates or synthetic mixtures containing coumarone and indene.

BACKGROUND OF THE INVENTION

Coumarone has been used in the preparation of synthetic resins, e.g., coumarone-indene resins, as a mixture because of the difficulty in separating indene and coumarone by conventional techniques like fractionation or crystallization. Coumarone has found use as a comonomer in other resins and, in high purity, as a monomer which forms an optically active polymer (*The Chemistry of Cationic Polymerization*, P. H. Plesch, Ed., 1963, The MacMillan Company, pp 449–450).

Previous methods for obtaining high purity coumarone, such as centrifugation, distillation and crystallization of coal tar distillates have not been particularly successful, although a chromatographic separation of indene with silica gel, activated alumina or activated carbon was disclosed in U.S. Pat. No. 2,930,821. Eluents or desorbents in the process included benzenes, lower alcohols, e.g., methanol or ethanol, carbon tetrachloride or other halogenated hydrocarbons, dioxane, nitrobenzene, steam, etc.

While recent developments indicate separation of indene from mixtures, including petrochemicals, such as crude oil fractions, e.g., naphtha, naphthalene; processed mixtures, e.g., naphtha cracker pyrolysis oil; synthetically-produced mixtures, e.g., dehydrogenation or cyclization reactions containing aromatics, by a chromatographic process, indene could not be obtained in purified form free of oxygenated compounds like coumarone, coumarone derivatives, such as methyl coumarone, etc., if they were present, because coumarone is coextracted with indene. In my previous U.S. Pat. No. 4,827,077 the preferred feeds were crude oil fractions, naphtha cracker pyrolysis oil and synthetically-produced aromatic mixtures that did not contain coumarone or other oxygenated compounds. However, the process of said patent could be practiced on feeds containing indene and coumarone if a practical way of separating coumarone from the feed thereof or from the product containing coextracted coumarone and indene could be found. Thus, it is an object of this invention to provide a method for removing coumarone from indene-containing feeds or from a product comprising a mixture of coumarone and indene obtained from another separation process in which the coumarone and indene are coextracted.

It is also known that crystalline aluminosilicates or zeolites are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type or silica are generally used.

The invention herein can be practiced in fixed or moving adsorbent bed systems or in cocurrent, pulsed batch systems described in U.S. Pat. No. 4,159,284, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well-known, but for reference thereto, Zinnen et al U.S. Pat. No. 4,642,397 is incorporated herein.

It is a further object of this invention to obtain coumarone in highly purified form by a highly selective chromatographic adsorption separation process from coumarone-indene mixtures, such as coal tar distillates.

It is a further object to provide a desorbent which will selectively desorb the coumarone from the adsorbent with sufficient resolution so as to obtain coumarone product with substantially reduced impurities and other feed materials. The preferred desorbents are ketones, esters and alcohols having a boiling point differing from the boiling range of the feed by at least about 5° C.

Other objects of the invention will be apparent from the following discussion.

SUMMARY OF THE INVENTION

In brief summary, the invention is, in a primary embodiment, a process for separating coumarone from a feed mixture comprising a coal tar distillate or a synthetically produced mixture containing coumarone and indene, which comprises contacting the mixture at adsorption conditions in an adsorption zone with an adsorbent exhibiting selectivity for the coumarone comprising a type X zeolite, the exchangeable cationic sites of which are exchanged with sodium, lithium or potassium ions, thereby selectively adsorbing the coumarone thereon and thereafter recovering a coumarone-rich extract by desorbing the coumarone, at desorption conditions with a desorbent comprising ketones, esters and alcohols. The raffinate contains indene and other saturated and unsaturated alkyl benzenes.

In another embodiment, coumarone is separated from a feed mixture containing indene, coumarone and one or more alkylbenzenes and/or other impurities by an adsorption separation process in which coumarone and indene are coextracted in a first stage separation, by contacting said feed mixture with a Y type zeolite exchanged with sodium or potassium to selectively adsorb coumarone and indene on said zeolite to the substantial exclusion of said alkylbenzenes and/or other impurities, recovering a coextract product with a type X zeolite adsorbent, the exchangeable cationic sites of which are exchanged with sodium, lithium or potassium, thereby selectively adsorbing the coumarone thereon and thereafter recovering a coumarone-rich extract by desorbing the coumarone, at desorption conditions, with a desorbent from the group previously mentioned. The first stage desorbent is preferably toluene, but may also be a halogenated aromatic such as fluorobenzene, benzene or another alkyl substituted monocyclic aromatic.

In the broadest aspect, however, the invention relates to a method for separating oxygenated compounds, such as coumarone, methyl coumarone, and other alkyl substituted benzofurans from feed streams containing indene, indane and alkyl- and unsaturated alkyl-substituted benzenes. Thereafter, the indene, which is a useful and valuable chemical for making polymers, can be separated from the remaining components by prior methods, such as disclosed in Zinnen U.S. Pat. No. 4,827,077.

Other embodiments of the invention encompass details about feed mixtures, adsorbents, desorbent materials and operating conditions, all of which are hereinafter disclosed in the following discussions of each of the facets of the present invention.

DETAILED DESCRIPTION OF THE INVENTION

Figure 1:
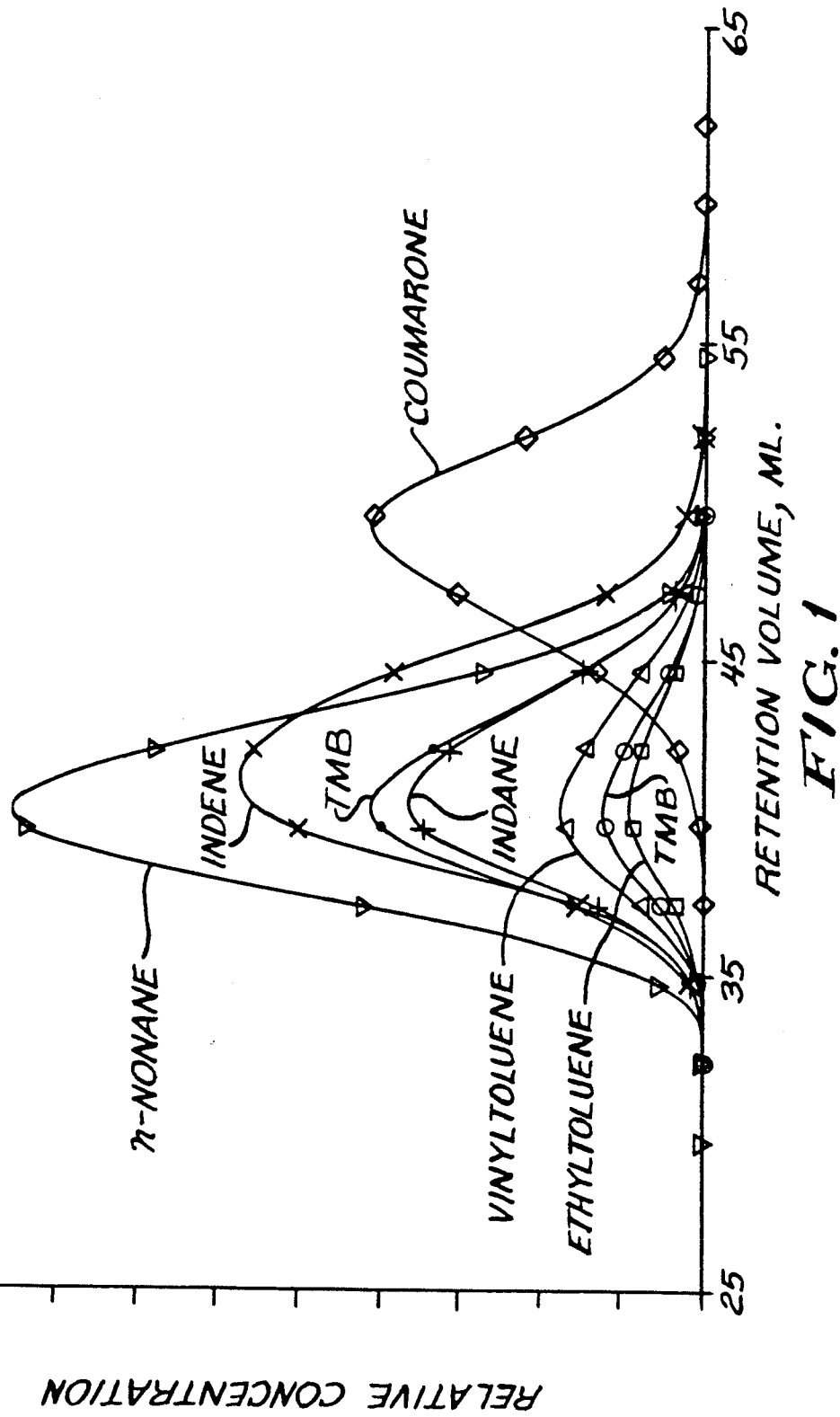
FIG. 1 is a chromatographic separation (pulse test) of a coumarone-containing feed mixture with a lithium-exchanged X zeolite and butyl acetate as the desorbent.

This invention relates to a process for separating coumarone from coumarone feed materials by adsorption chromatography, utilizing Na-, Li- or K-exchanged X or Y zeolites, in conjunction with an appropriate desorbent.

Adsorbents to be used in the process of this invention comprise specific crystalline aluminosilicates or molecular sieves, namely X and Y zeolites. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction of the different isomers and the adsorbent rather than on pure physical size differences in the isomer molecules.

In hydrated form, the preferred crystalline aluminosilicates generally encompass those zeolites represented by the formula 1 below:

$$M_{2/n}O:Al_2O_3:wSiO_2:yH_2O \qquad \text{Formula 1}$$

where "M" is a cation which balances the electrovalence of the tetrahedra and is generally referred to as an exchangeable cationic site, "n" represents the valence of the cation, "w" represents the moles of SiO$_2$, and "y" represents the moles of water. The cations may be any one of a number of cations which will hereinafter be described in detail.

Adsorbents comprising the type X and type Y zeolites are useful for the adsorptive process for separating coumarone and indene herein described. These zeolites are described and defined in U.S. Pat. Nos. 2,882,244 and 3,130,007, respectively. The terms "type X-structured" and "type Y-structured" zeolites as used herein shall include all zeolites which have general structures as represented in the above two cited patents.

The type X- and Y-structured zeolites in the hydrated or partially hydrated form can be represented in terms of moles of metal oxides as shown in Formulas 2 and 3, respectively, below:

$$(0.9 \pm 0.2)M_{2/n}O:Al_2O_3:(2.5 \pm 0.5)SiO_2:yH_2O \qquad \text{Formula 2}$$

$$(0.9 \pm 0.2)M_{2/n}O:Al_2O_3:wSiO_2:yH_2O \qquad \text{Formula 3}$$

where "M" represents at least one cation having a valence of not more than 3, "n" represents the valence of "M", "w" is greater than 3.0 up to about 6 and "y" is a value up to about 9 depending upon the identity of "M" and the degree of hydration of the crystal.

The terms "type X zeolite" and "type Y zeolite" as employed herein shall refer not only to a type X-structured and type Y-structured zeolites containing sodium, lithium and potassium cations as the cation "M" indicated in the formulas above, but also shall refer to those containing other additional cations in Group IA of the Periodic Table of Elements. Typically both the type X and type Y structured zeolites as initially prepared are predominantly in the sodium form. The term "exchanged cationic site" generally refers to the site in the zeolite occupied by the cation "M". This cation, usually sodium, can be replaced or exchanged with other specific cations, such as those mentioned above, depending on the type of the zeolite to modify characteristics of the zeolite. The preferred zeolite for use in this invention is a type X zeolite exchanged with sodium cations, i.e., in the form as prepared, lithium or potassium ions, and type Y zeolite exchanged with sodium ions.

Cations occupying exchangeable cationic sites in the zeolite are exchanged with other cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, then dried to a desired water content. By such methods, the sodium cations and any non-sodium cations which might be occupying exchangeable sites are impurities in a sodium-X or sodium-Y zeolite can be partially or essentially completely replaced with other cations. It is preferred that the zeolite used in the process of this invention contain cations at exchangeable cationic sites selected from the group consisting of the alkali metals and particularly sodium, lithium and potassium.

Typically, adsorbents used in separative processes contain the crystalline material dispersed in an amorphous inorganic matrix or binder, having channels and cavities therein which enable liquid access to the crystalline material. Amorphous material such as silica, or silica-alumina mixtures or compounds, such as clays, are typical of such inorganic matrix materials. The binder aids in forming or agglomerating the crystalline particles of the zeolite which otherwise would comprise a fine powder. The adsorbent may thus be in the form of particles such as extrudates, aggregates, tablets, macrospheres or granules having a desired particle size range, from about 16 to about 40 mesh (Standard U.S. Mesh) (1.9 MM TO 250$\mu$).

Feed mixtures which can be used in the process of the invention include coal tar naphtha and fractionated coal tar naphthas. A typical composition for a coal tar naphtha and distillates thereof derived by fractionation in a 20 plate column are exemplified by the following:

TABLE 1

| Component | Coal Tar Naphtha (wt. %) | Coal Tar Naphtha Distillates | | |
|---|---|---|---|---|
| | | (wt. %) (154–161° C.) | (wt. %) (173–177° C.) | (wt. %) (183–187° C.) |
| BTX(1) | 21.7 | — | — | — |
| Trimethylbenzenes | 4.8 | 30 | 17.8 | 0.5 |
| Ethyltoluenes | 0.7 | 11.6 | 4.7 | — |
| Unsaturated | | | | |
| Alkylbenzenes | 6.5 | 7.0 | 9.4 | 2.1 |
| Coumarone | 3.3 | 12.1 | 16.8 | — |
| Indane | 3 | 2.9 | 12.5 | 2.1 |
| Indene | 49.7 | 5.8 | 35.2 | 76.8 |
| Methyl Coumarone & Methyl Indene | 1.5 | — | — | 8.1 |
| Naphthalene | 2 | — | — | — |
| Other | 6.8 | 30.6 | 3.6 | 12.5 |

(1) Benzene, Toluene, Xylenes

Analysis of the distillates by gas chromatography/mass spectroscopy shows that the unsaturated alkylbenzenes include compounds such as styrene, alpha-methyl styrene, beta-methyl styrene, vinyl toluene and propenylbenzene.

A suitable desorbent or desorbents for a particular separation with a specific adsorbent are not always predictable. In the preferred isothermal, isobaric, liquid-phase operation of the process of my invention, I have found that desorbent materials comprising ketones, alcohols, and esters, selected to differ in boiling point by at least 5° C. from the boiling range of the feedstock so the desorbent may be recovered for reuse, will result in selectivity for coumarone or a coumarone-indene coextracted product when used with the above discussed adsorbents. In a practical application, such as shown in the examples, where the feed has a boiling point range of about 173°–176° C., the preferred desorbent will be selected from the above mentioned groups, and have a boiling point below about 168° C. or above about 181° C. Among the ketones that can be used are n-alkyl ketones, such as diethyl ketone and methyl ethyl ketone, methyl butyl ketone, 2-pentanone, 3-hexanone, 2- and 3-heptanone, etc. Singly branched alkyl ketones, e.g., methyl isopropylketone, methyl isobutyl ketone and other $C_6$–$C_8$ or higher ketones. Although branching generally lowers the boiling point of the desorbent and ketones with greater branching may be suitable as a desorbent, one di-branched alkyl ketone, diisopropylketone, was found to be too weak as a desorbent to remove coumarone from an X zeolite. However, indene can be desorbed by diisopropylketone. Failure of diisopropylketone to desorb coumarone may be due to steric influences.

Alcohols which may be used include $C_6$–$C_8$ or higher alcohols such as n-hexanol, 2-hexanol, 1- and 2-heptanol, 1-and 2-octanol, etc.

Esters that can be used as desorbents in the process include n-butyl acetate, sec-butyl acetate, t-butyl acetate, n-butyl propionate, sec-butyl propionate, butyl butyrate, sec-butyl butyrate or other esters containing 6 to 8 or greater carbons. Certain combinations of adsorbent and desorbent which were found to be most effective in the separations disclosed herein are indicated in the examples.

When the feed mixture contains indenes, coumarones or other oxygenates and other alkylbenzenes, it may be preferable to proceed in two stages: in the first stage, obtain an extract material, for example, using the process disclosed in the aforesaid U.S. Pat. No. 4,827,077, containing coumarone and indene and, in a second stage, separating the coumarone from indene by the present process.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° to about 200° C. and a pressure sufficient to maintain liquid phase, ranging from about atmospheric to about 500 psig. Desorption conditions will include the same range of temperatures and pressures as used for adsorption conditons.

At least a portion of the extract stream, and preferably at least a portion of the raffinate stream, from the separation process are passed to separation means, typically fractionators or evaporators, where at least a portion of the desorbent material is separated to produce an extract product and a raffinate product, respectively.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of the feed mixture is injected for a duration of several minutes. Desorbent flow is resumed, and the coumarone (or coumarone-indene coextract) and other components are eluted as in a liquid-solid chromatographic operation. The effluent can be analyzed on stream or alternatively, effluent samples can be collected periodically and later analyzed separately by analytical equipment and traces of the envelopes of corresponding component peaks developed.

From information derived from the test, adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, ($\beta$) for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The following examples are presented to illustrate the selectivity relationship that makes the process of this invention possible. The examples are not intended to unduly restrict the scope of the claims.

EXAMPLE I

The purpose of this example is to present the results of a pulse test obtained from the above described pulse test apparatus when using a lithium-exchanged X (Li-X) zeolite at 150° C. with 30/70 butyl acetate/n-C$_7$ mixture as desorbent-one of the preferred adsorbent-desorbent combinations, to separate and recover coumarone from a coumarone-containing complex coal tar distillate mixture.

The coal tar distillation fraction (b.p. 173°–177° C.) from Table 1 was used as the feed mixture.

A feed pulse consisting of 1.4 cc of the above coal tar distillate and 0.6 cc n-heptane tracer was introduced to the pulse test column at 150° C., which was packed with LiX adsorbent. A 30/70 mixture (wt. %) of butyl acetate and n-heptane was used as the desorbent material at a flow rate of 1.24 ml/min.

From the plot of relative concentration (by gas chromatographic area counts) vs. retention volume (RV) in ml. shown in FIG. 1, selectivities calculated among the various groups of compounds and coumarone are set forth in the following Table 2 (where GRV is gross retention volume, NRV is net retention volume, $\beta$ is the selectivity of each component with respect to the reference component, coumarone):

TABLE 2

| Component | GRV | NRV | $\beta$ |
|---|---|---|---|
| n-C$_9$ | 40.5 | 0.0 | tracer |
| Trimethylbenzene (TMB) | 40.7 | 0.2 | >10 |
| Trimethylbenzene (TMB) | 40.8 | 0.3 | >10 |
| Ethyltoluene | 40.9 | 0.4 | >10 |
| Vinyltoluene | 40.9 | 0.4 | >10 |
| Indane | 41.0 | 0.5 | >10 |
| Indene | 41.9 | 1.4 | 6.15 |
| Coumarone | 49.0 | 8.5 | Ref. |

EXAMPLE II

Figure 2:
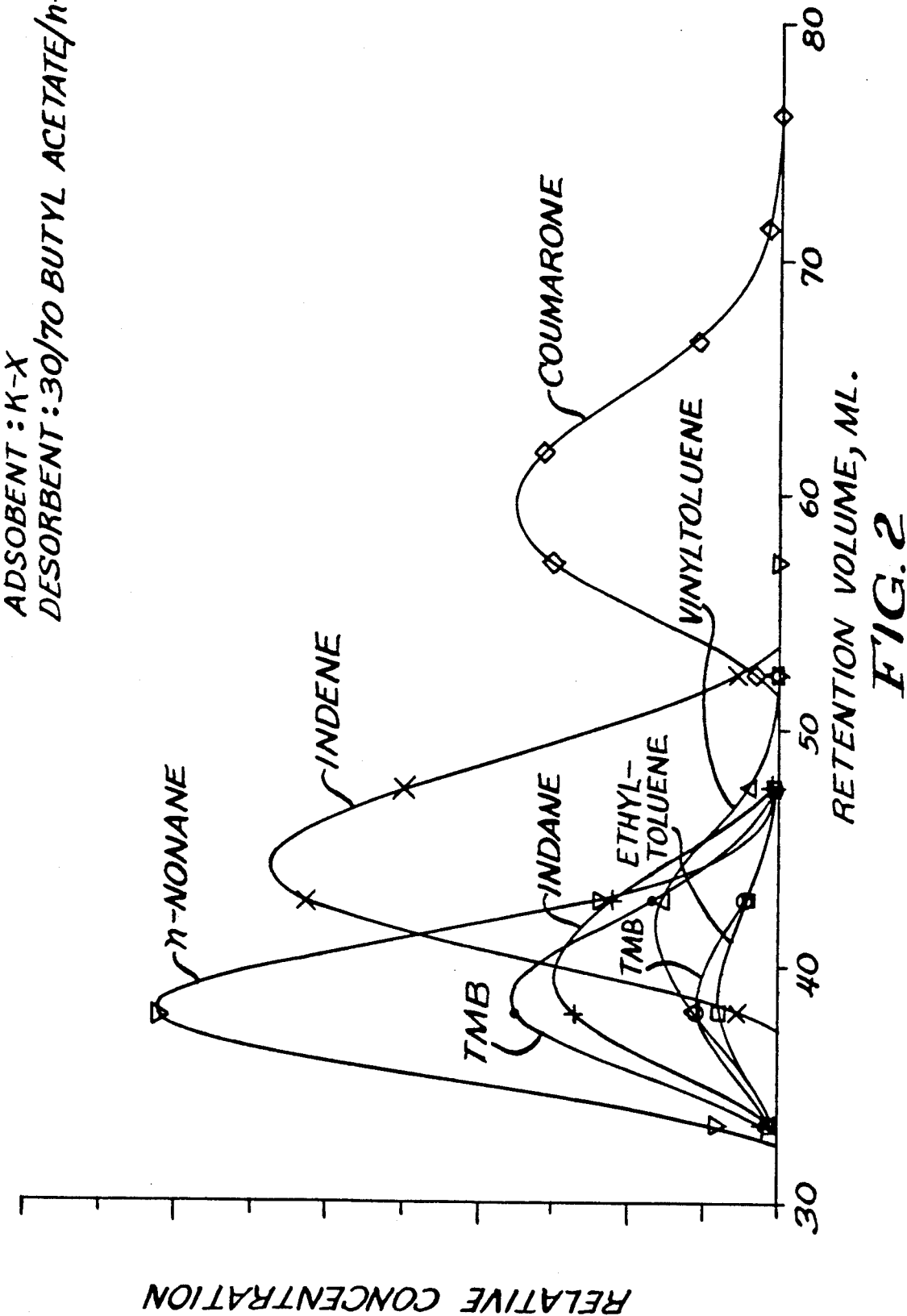
FIG. 2 is similar to FIG. 1 except that K-X zeolite was used as the adsorbent.

The pulse test of Example I was repeated on the same feed using a different adsorbent, K-X zeolite. The desorbent was a 30/70 mixture of butylacetate and n-nonane (n-C$_9$). This adsorbent-desorbent combination is one of the preferred combinations. The results are shown in FIG. 2 and the following Table 3:

TABLE 3

| Component | GRV | NRV | $\beta$ |
|---|---|---|---|
| n-C$_9$ | 38.4 | 0.0 | 0.00 |
| Trimethylbenzene (TMB) | 38.8 | 0.4 | >10 |
| Trimethylbenzene (TMB) | 39.1 | 0.7 | >10 |
| Ethyltoluene | 39.2 | 0.7 | >10 |
| Vinyltoluene | 41.3 | 2.9 | 7.50 |
| Indane | 40.2 | 1.8 | >10 |
| Indene | 44.9 | 6.5 | 3.34 |
| Coumarone | 60.1 | 21.6 | 1.00 |

In another pulse test on the same feed, with a K-X zeolite as the adsorbent, but using a 30/70 wt. %/wt. % mixture of methyl isobutylketone (MIBK)/n-heptane (n-C$_7$) as desorbent, the results were as shown in the following Table 4.

TABLE 4

| Component | GRV | NRV | $\beta$ |
|---|---|---|---|
| n-C$_9$ | 35.0 | 0.0 | 0.00 |
| Trimethylbenzene (TMB) | 35.7 | 0.7 | >10 |
| Trimethylbenzene (TMB) | 36.1 | 1.1 | >10 |
| Ethyltoluene | 36.0 | 1.0 | >10 |
| Vinyltoluene | 41.1 | 6.1 | 7.11 |
| Indane | 38.4 | 3.4 | >10 |
| Indene | 50.0 | 15.0 | 2.88 |
| Coumarone | 78.3 | 43.3 | 1.00 |

In a third pulse test at 100° C. and with the same feed, using instead a Na-X zeolite as the adsorbent and a 30/70 mixture (by wt.) of butyl acetate/n-C$_7$ as the desorbent, the results were as follows:

TABLE 5

| Component | GRV | NRV | $\beta$ |
|---|---|---|---|
| n-C$_9$ | 50.1 | 0.0 | 0.00 |
| Trimethylbenzene (TMB) | 50.1 | 0.0 | — |
| Trimethylbenzene (TMB) | 50.2 | 0.1 | >10 |
| Ethyltoluene | 50.2 | 0.11 | >10 |

TABLE 5-continued

| Component | GRV | NRV | β |
|---|---|---|---|
| Vinyltoluene | 50.4 | 0.3 | >10 |
| Indane | 50.3 | 0.2 | 27.02 |
| Indene | 51.0 | 0.9 | 6.12 |
| Coumarone | 55.6 | 5.5 | 1.00 |

In the second and third pulse tests above, considerably more tailing of the extract product, coumarone, was evident, indicating a less desirable process from a practical, commercial viewpoint. However, in each of the separations of this example, since coumarone is the most strongly adsorbed component, and indene the next most strongly adsorbent component, coumarone can be extracted as the product in a first stage of a two-stage process and indene can be extracted in the second stage, using the same combination of adsorbent and desorbent as the first stage in both stages or by the process disclosed in the aforementioned U.S. Pat. No. 4,827,077.

EXAMPLE III

Another pulse test was run like Example I on the same feed, except that Na-X was the adsorbent and hexanol was the desorbent admixed with 70% n-$C_7$ and T=100° C. Good separation was achieved as shown in the following table of results.

TABLE 6

| Component | GRV | NRV | β |
|---|---|---|---|
| n-$C_9$ | 43.0 | 0.0 | tracer |
| Trimethylbenzene (TMB) | 43.1 | 0.1 | >10 |
| Trimethylbenzene (TMB) | 43.1 | 0.1 | >10 |
| Ethyltoluene | 43.2 | 0.2 | >10 |
| Vinyltoluene | 43.4 | 0.4 | 7.86 |
| Indane | 43.2 | 0.2 | >10 |
| Indene | 43.5 | 1.5 | 6.29 |
| Coumarone | 46.3 | 3.3 | Ref. |

EXAMPLE IV

Figure 3:
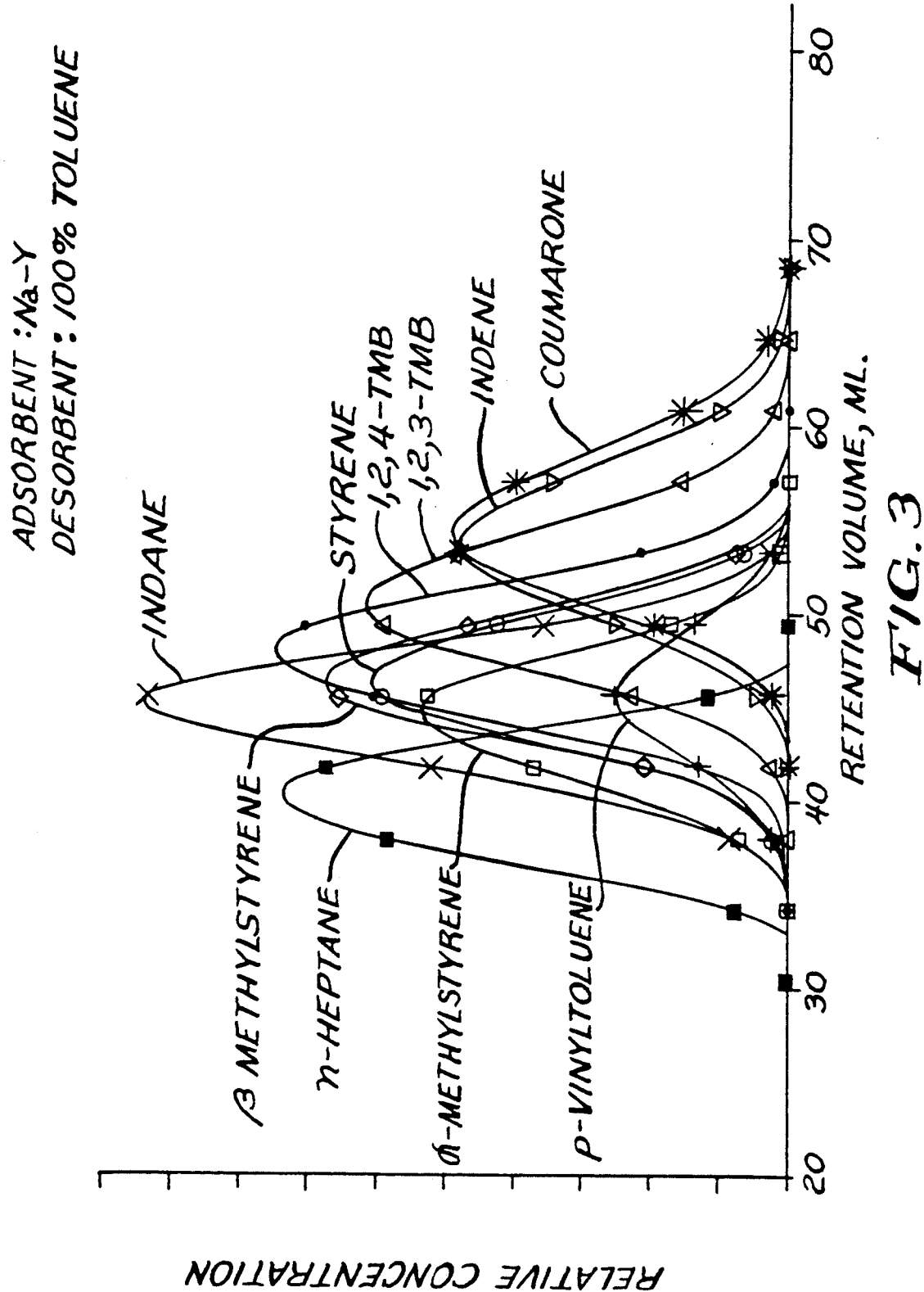
FIG. 3 is a chromatographic separation of a coumarone-indene coextract from a feed mixture also containing various alkyl-substituted and alkenyl-substituted benzenes with Na-Y zeolite and toluene as the desorbent.

Another pulse test was run in which the adsorbent was sodium-exchanged Y zeolite and the desorbent was toluene. The feed was a synthetic feed containing 0.5 gm each of coumarone, indene, indane, and the following alkyl benzenes and unsaturated alkyl-substituted benzenes: 1,2,4-trimethyl benzene (1,2,4-TMB); 1,2,3-trimethyl benzene (1,2,3-TMB), styrene; α-methyl styrene; β-methyl styrene and p-vinyltoluene. The process was conducted at 150° C. with column flow rate of 1.14 cc/min. Coumarone and indene were coextracted while the other components were relatively non-adsorbed and collected as raffinate. The results are shown in FIG. 3 and the following table.

TABLE 7

| Component | GRV | NRV | β |
|---|---|---|---|
| n-$C_7$ | 40.1 | 0.0 | 0.00 |
| Styrene | 46.7 | 6.6 | 2.09 |
| 1,2,4-TMB | 47.8 | 7.7 | 1.78 |
| Methylstyrene | 44.4 | 4.3 | 3.21 |
| 1,2,3-TMB | 50.9 | 10.7 | 1.28 |
| P-Vinyltoluene | 45.8 | 5.6 | 2.44 |
| Indane | 45.0 | 4.9 | 2.82 |
| β-Methylstyrene | 46.8 | 6.7 | 2.07 |
| Indene | 53.9 | 13.8 | 1.00 |
| Coumarone | 54.7 | 14.6 | 0.94 |

This experiment illustrates the co-extraction of indene and coumarone from a complex mixture containing alkyl and unsaturated alkyl benzenes.

A coumarone-indene feed mixture, similar to the co-extract from the above separation can be separated by the process of this invention by contacting the extract as the feed to a second-stage pulse test with a sodium-exchanged X zeolite adsorbent. In this simulated example, the feed mixture will comprise 1.5 ml of the coumarone-indene mixture, 0.3 ml n-$C_7$ and 0.5 ml of diethylketone (DEK). The more strongly adsorbed component, coumarone, will be desorbed with DEK. The results of such a separation are shown in the following Table 8, which data are identical to that found for these components in Table 9 and are obtained from the experiments described in Example V.

TABLE 8

| Component | GRV | NRV | β |
|---|---|---|---|
| n-$C_7$ | 42.2 | 0.0 | tracer |
| Indene | 42.7 | 0.5 | 10.65 |
| Coumarone | 46.8 | 4.6 | Ref. |

EXAMPLE V

Figure 4:
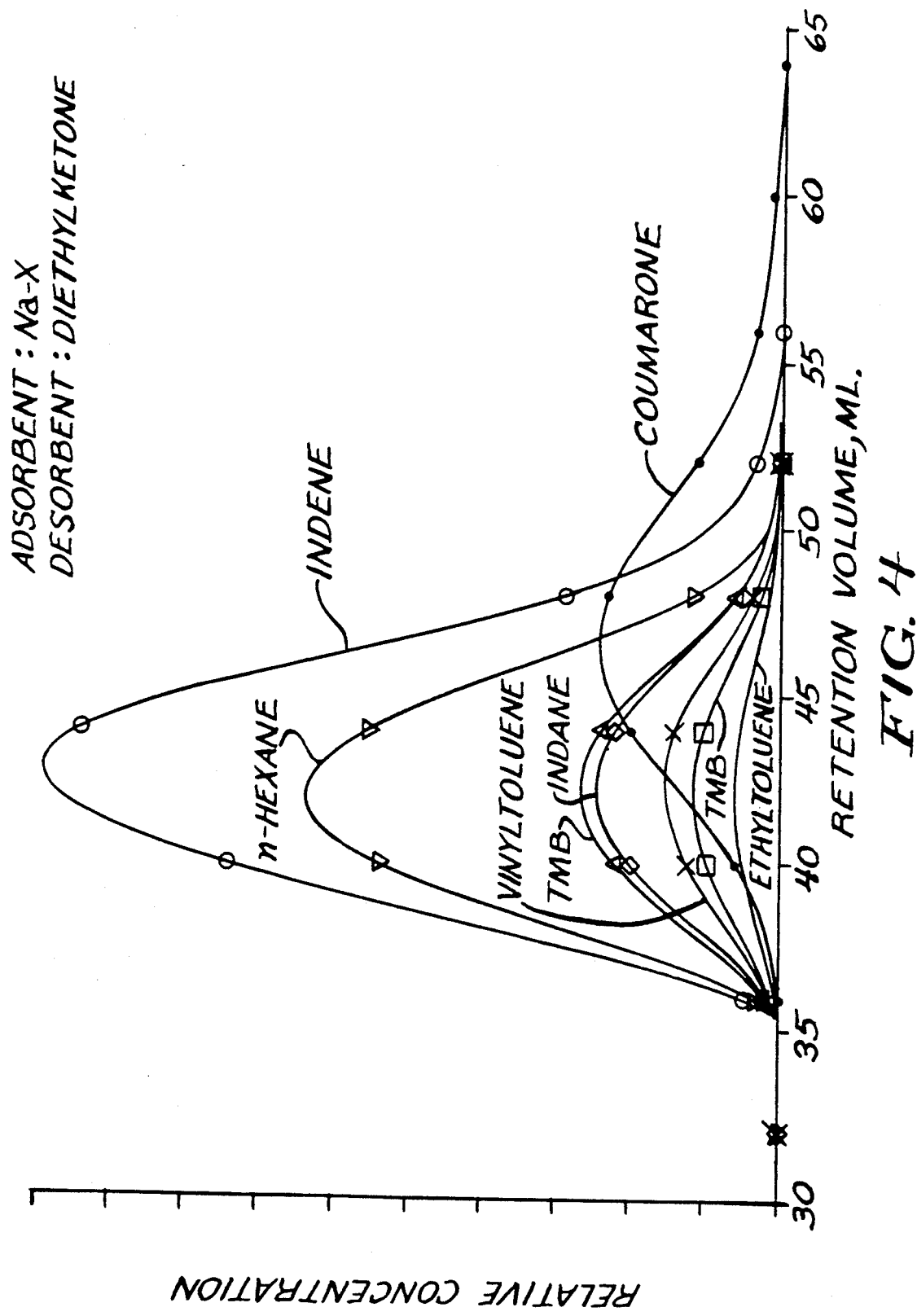
FIG. 4 is a chromatographic separation of coumarone from indene, indane and alkyl benzenes with Na-X zeolite and diethylketone as the desorbent.

Another pulse test was run in which the adsorbent was sodium exchanged X zeolite and the desorbent was diethylketone. The feed was a coal tar naphtha distillate (b.p. 173°-176° C.) with the following composition: ethyltoluenes 4.9%, trimethylbenzenes 15.6%, unsaturated alkyl benzenes 7.8%, indane 10.1%, indene 42%, coumarone 12.6%. The temperature was 55° C. The results are shown in FIG. 4 and Table 9.

TABLE 9

| Component | GRV | NRV | β |
|---|---|---|---|
| n-$C_7$ | 42.2 | 0 | tracer |
| Trimethylbenzene (TMB) | 42.3 | 0.1 | >10 |
| Trimethylbenzene (TMB) | 42.4 | 0.2 | >10 |
| Ethyltoluene | 42.3 | 0.1 | >10 |
| Vinyltoluene | 42.4 | 0.2 | >10 |
| Indane | 42.4 | 0.2 | >10 |
| Indene | 42.7 | 0.5 | >10 |
| Coumarone | 46.9 | 4.6 | Ref. |

What is claimed is:

1. A process for removing oxygenated compounds from a feed mixture containing at least one oxygenated compound, indene and alkyl-substituted benzenes comprising contacting said feed mixture at adsorption conditions with an X-type zeolite exchanged with Group IA ions to selectively adsorb said oxygenated compounds and recovering said oxygenated compounds by desorption at desorption conditions with a polar desorbent selected from the group consisting of ketones, alcohols and esters which differ in boiling point from the feed boiling range by at least 5° C., said adsorption conditions and desorption conditions selected from a temperature from about 20° to about 200° C. and a pressure sufficient to maintain liquid phase.

2. The process of claim 1 wherein said feed mixture is a coal tar distillate.

3. The process of claim 1 wherein said oxygenated compound comprises coumarone or a coumarone derivative.

4. The process of claim 1 wherein said feed is a fraction of a petrochemical material.

5. The process of claim 1 wherein said feed is a synthetically-derived organic material.

6. The process of claim 1 wherein said feed additionally contains indane.

7. The process of claim 2 wherein said oxygenated compound comprises coumarone and said mixture is first contacted with a Y-type zeolite exchanged with Na ions to selectively adsorb said coumarone and indene and desorbing said coumarone and indene as a coextract product with a second desorbent.

8. The process of claim 7 wherein said second desorbent is toluene.

9. The process of claim 7 wherein said second desorbent is fluorobenzene.

10. The process of claim 1 wherein said feed mixture contains one or more alkyl-substituted benzenes.

11. The process of claim 10 wherein said alkyl substituent may be saturated or unsaturated alkyl.

12. The process of claim 1 wherein said adsorbent is Li-X and said desorbent is butyl acetate.

13. The process of claim 1 wherein said adsorbent is K-X and said desorbent is butyl acetate.

14. The process of claim 1 wherein said adsorbent is Na-X and said desorbent is diethylketone.

15. A process for separating coumarone from a feed mixture containing coumarone comprising contacting said feed mixture at adsorption conditions with an X-type zeolite exchanged with Group IA ions to selectively adsorb coumarone and recovering said coumarone by desorption at desorption conditions with a polar desorbent selected from the group consisting of ketones, alcohols and esters which have boiling points differing by at least 5° C. from the boiling point range of said feed mixture, said adsorption conditions and desorption conditions selected from a temperature from about 20° to about 200° C. and a pressure sufficient to maintain liquid phase.

16. A process for coextracting a mixture of coumarone and indene from a feed containing coumarone, indene, alkyl benzenes and unsaturated alkyl benzenes comprising contacting said feed with a Y-type zeolite adsorbent having sodium ions at the exchangeable ion sites to selectively adsorb said coumarone and indene and recovering a mixture of coumarone and indene by desorption with a desorbent comprising toluene.

* * * * *